US010163223B2

(12) United States Patent
Tachibana

(10) Patent No.: US 10,163,223 B2
(45) Date of Patent: Dec. 25, 2018

(54) AUTOMATIC ANALYSER

(71) Applicant: HITACHI HIGH-TECHNOLOGIES CORPORATION, Tokyo (JP)

(72) Inventor: Shinji Tachibana, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/552,501

(22) PCT Filed: Feb. 5, 2016

(86) PCT No.: PCT/JP2016/053565
§ 371 (c)(1),
(2) Date: Aug. 22, 2017

(87) PCT Pub. No.: WO2016/136435
PCT Pub. Date: Sep. 1, 2016

(65) Prior Publication Data
US 2018/0012375 A1 Jan. 11, 2018

(30) Foreign Application Priority Data

Feb. 24, 2015 (JP) .................................. 2015-033821

(51) Int. Cl.
*G06T 15/20* (2011.01)
*G06K 9/00* (2006.01)
(Continued)

(52) U.S. Cl.
CPC ............... *G06T 7/73* (2017.01); *G01N 35/00* (2013.01); *G01N 35/00732* (2013.01);
(Continued)

(58) Field of Classification Search
CPC . G06T 2207/30208; G06T 7/73; G06T 15/20; G01N 35/00; G01N 2035/00752;
(Continued)

(56) References Cited

U.S. PATENT DOCUMENTS

2004/0265173 A1* 12/2004 Matsumoto .......... G01N 35/025
422/64
2008/0285854 A1 11/2008 Kotake et al.

FOREIGN PATENT DOCUMENTS

EP 3 200 118 A1 8/2017
ES 2 529 514 A 2/2015
(Continued)

OTHER PUBLICATIONS

International Search Report for PCT/JP2016/053565 dated Apr. 5, 2016.
(Continued)

*Primary Examiner* — Kim Vu
*Assistant Examiner* — Michael Vanchy, Jr.
(74) *Attorney, Agent, or Firm* — Mattingly & Malur, PC

(57) ABSTRACT

A two-dimensional code is attached to a location of a reagent storage unit which is visually recognizable from the outside, and a coordinate position of the two-dimensional code in a coordinate system of the two-dimensional code and coordinate information of an installation position of a reagent bottle are held. After that, an image of the two-dimensional code is captured by a portable terminal so that a coordinate system of an image capture unit of the portable terminal is converted into the coordinate system of the two-dimensional code using AR technology. The coordinate information of the installation position of the reagent bottle in the coordinate system of the two-dimensional code is regarded as positional coordinates in the captured image on the basis of the conversion, thereby ascertaining the position of the reagent bottle on the captured image and displaying the ascertained position on a display unit.

3 Claims, 12 Drawing Sheets

(51) Int. Cl.
   *G01N 35/08*    (2006.01)
   *G06T 7/73*     (2017.01)
   *G01N 35/00*    (2006.01)
   *G06K 7/14*     (2006.01)
   *G06T 7/00*     (2017.01)
   *G06K 7/10*     (2006.01)
   *G06K 9/20*     (2006.01)
   *G06T 19/00*    (2011.01)
   *G01N 35/04*    (2006.01)

(52) U.S. Cl.
   CPC .......... *G01N 35/08* (2013.01); *G06K 7/1094* (2013.01); *G06K 7/10544* (2013.01); *G06K 7/1443* (2013.01); *G06K 7/1447* (2013.01); *G06K 9/00214* (2013.01); *G06K 9/00671* (2013.01); *G06T 7/00* (2013.01); *G06T 15/20* (2013.01); *G01N 2035/00673* (2013.01); *G01N 2035/00782* (2013.01); *G01N 2035/0443* (2013.01); *G06K 7/10376* (2013.01); *G06K 7/10881* (2013.01); *G06K 9/2063* (2013.01); *G06T 19/006* (2013.01); *G06T 2207/30208* (2013.01)

(58) Field of Classification Search
   CPC ... G01N 2035/0406; G01N 2035/0458; G01N 2035/1088; G01N 35/00732; G01N 35/025; G01N 35/04; G06K 7/10871; Y10T 436/11; Y10T 436/113332; B01L 2300/021; B01L 3/5453
   See application file for complete search history.

(56) References Cited

FOREIGN PATENT DOCUMENTS

| JP | 3314629      | 6/2002  |
|----|--------------|---------|
| JP | 2008-065807  | 3/2008  |
| JP | 2009-250743  | 10/2009 |
| JP | 2011-112524  | 6/2011  |

OTHER PUBLICATIONS

International Preliminary Report on Patentability received in corresponding International Application No. PCT/JP2016/053565 dated Sep. 8, 2017.
Extended European Search Report received in corresponding European Application No. 16755184.5 dated Aug. 21, 2018.

* cited by examiner

[Fig. 1]
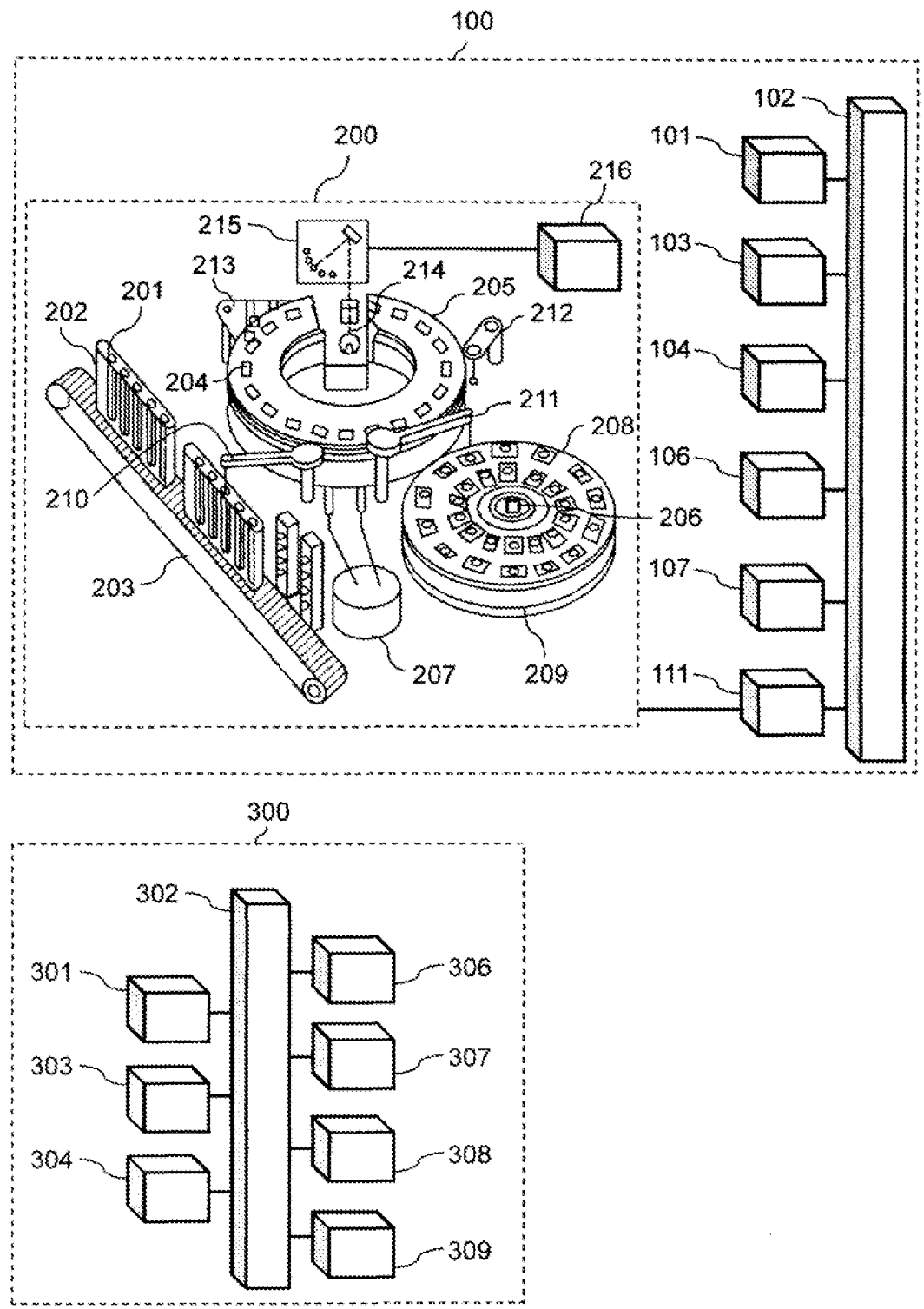

[Fig. 2]
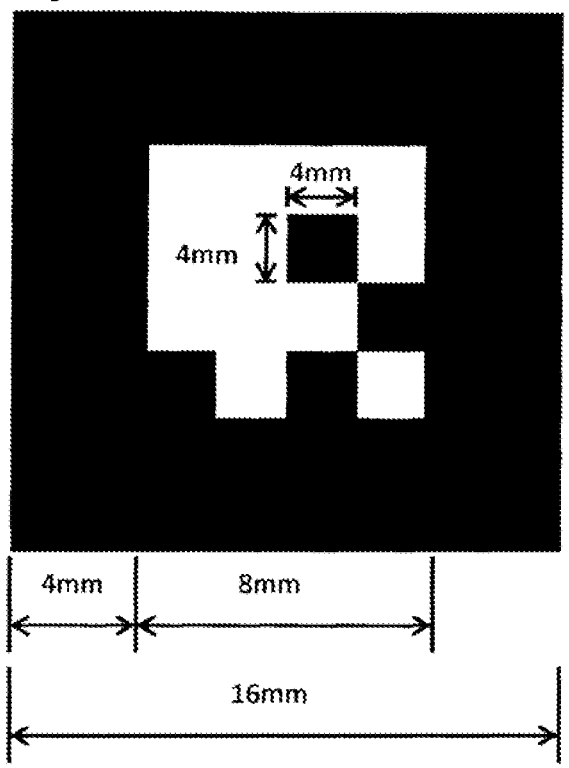

[Fig. 3]
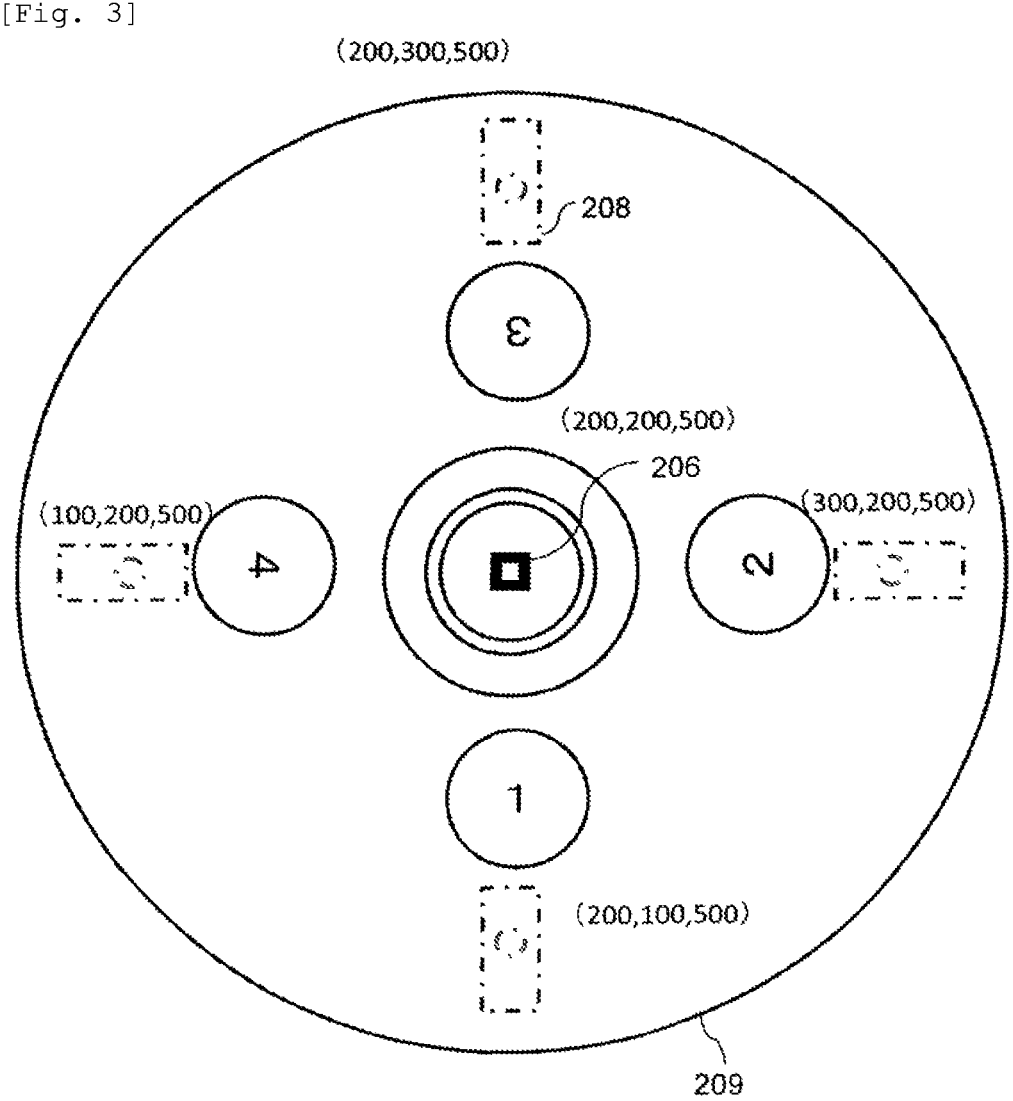

[Fig. 4]
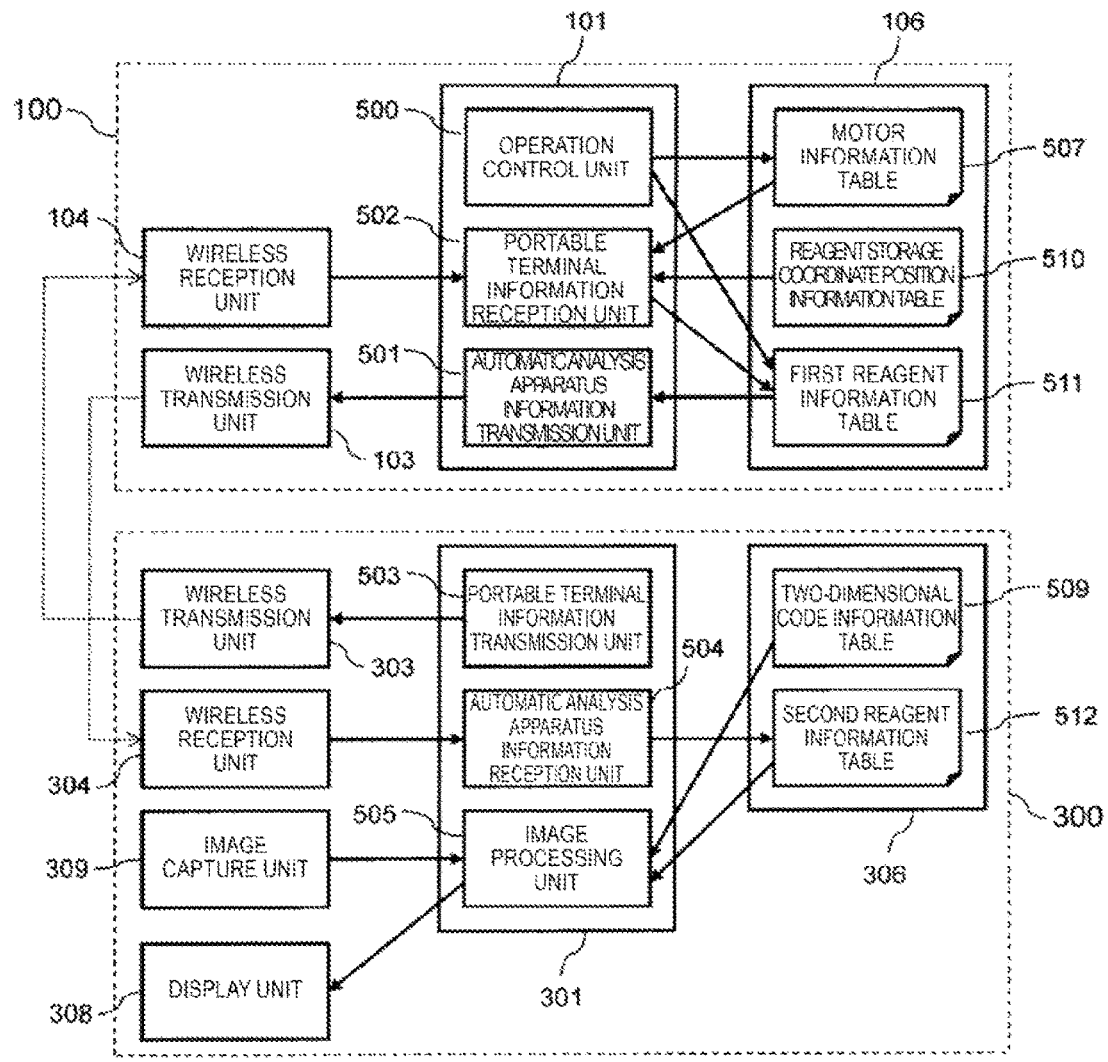
[Fig. 5]
| MOTOR NUMBER | MOTOR NAME | ROTATION ANGLE [DEGREE] |
|---|---|---|
| Mo1 | REAGENT STORAGE UNIT ROTATION | 0 \| 90 \| 180 \| 270 |

[Fig. 6]
| REAGENT STORAGE UNIT REAGENT INSTALLATION POSITION NUMBER | COORDINATE POSITION X, Y, Z |
|---|---|
| 1 | 200,100,500 |
| 2 | 300,200,500 |
| 3 | 200,300,500 |
| 4 | 100,200,500 |
[Fig. 7]
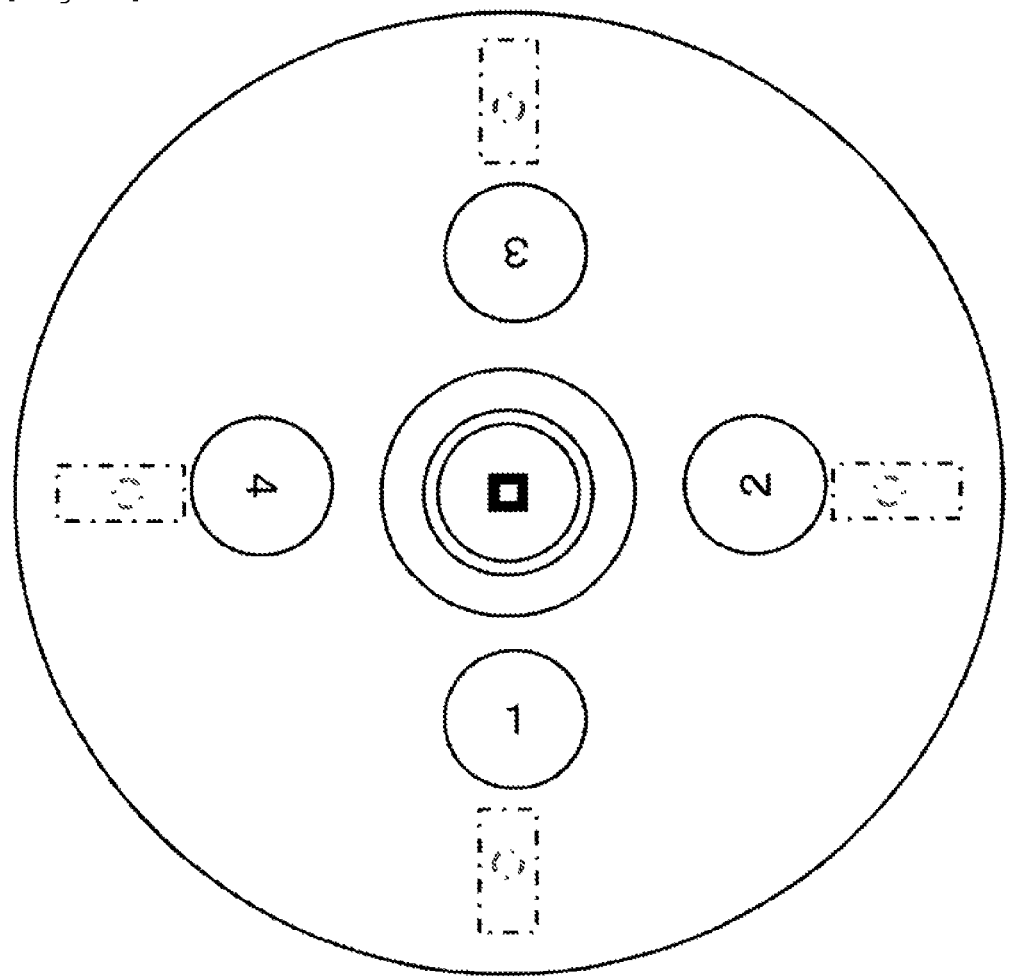

[Fig. 8]
| REAGENT STORAGE UNIT REAGENT INSTALLATION POSITION NUMBER | COORDINATE POSITION X, Y, Z |
|---|---|
| 1 | 100,200,500 |
| 2 | 200,100,500 |
| 3 | 300,200,500 |
| 4 | 200,300,500 |
[Fig. 9]
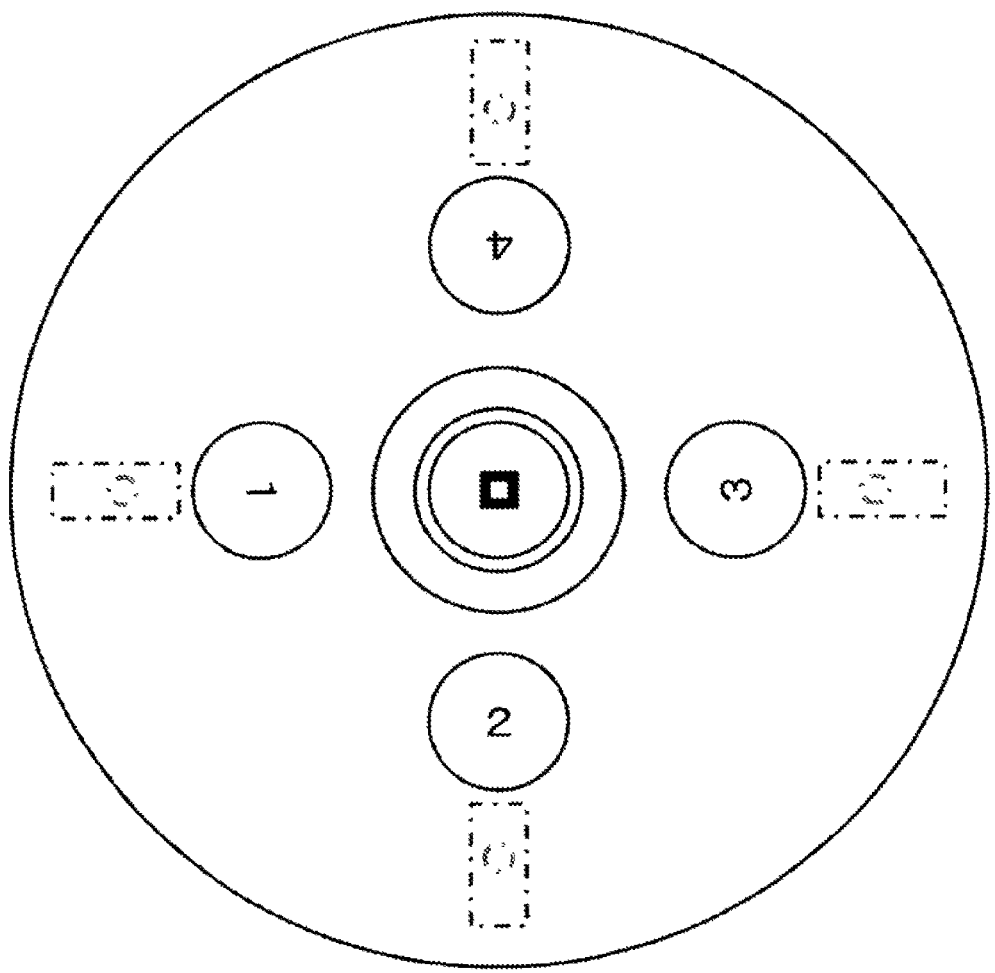

[Fig. 10]
| REAGENT STORAGE UNIT REAGENT INSTALLATION POSITION NUMBER | COORDINATE POSITION X, Y, Z |
|---|---|
| 1 | 200,300,500 |
| 2 | 100,200,500 |
| 3 | 200,100,500 |
| 4 | 300,200,500 |
[Fig. 11]
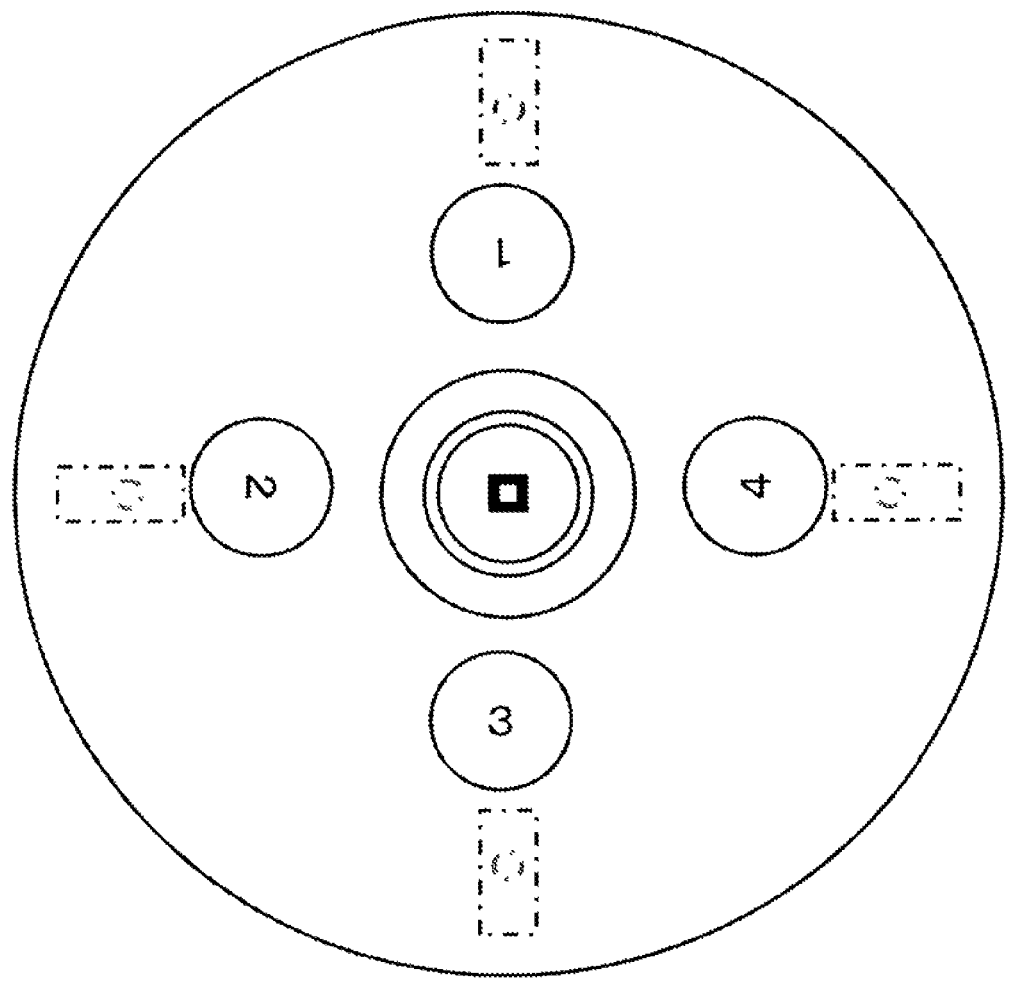

[Fig. 12]
| REAGENT STORAGE UNIT REAGENT INSTALLATION POSITION NUMBER | COORDINATE POSITION X, Y, Z |
|---|---|
| 1 | 300,200,500 |
| 2 | 200,300,500 |
| 3 | 100,200,500 |
| 4 | 200,100,500 |
[Fig. 13]
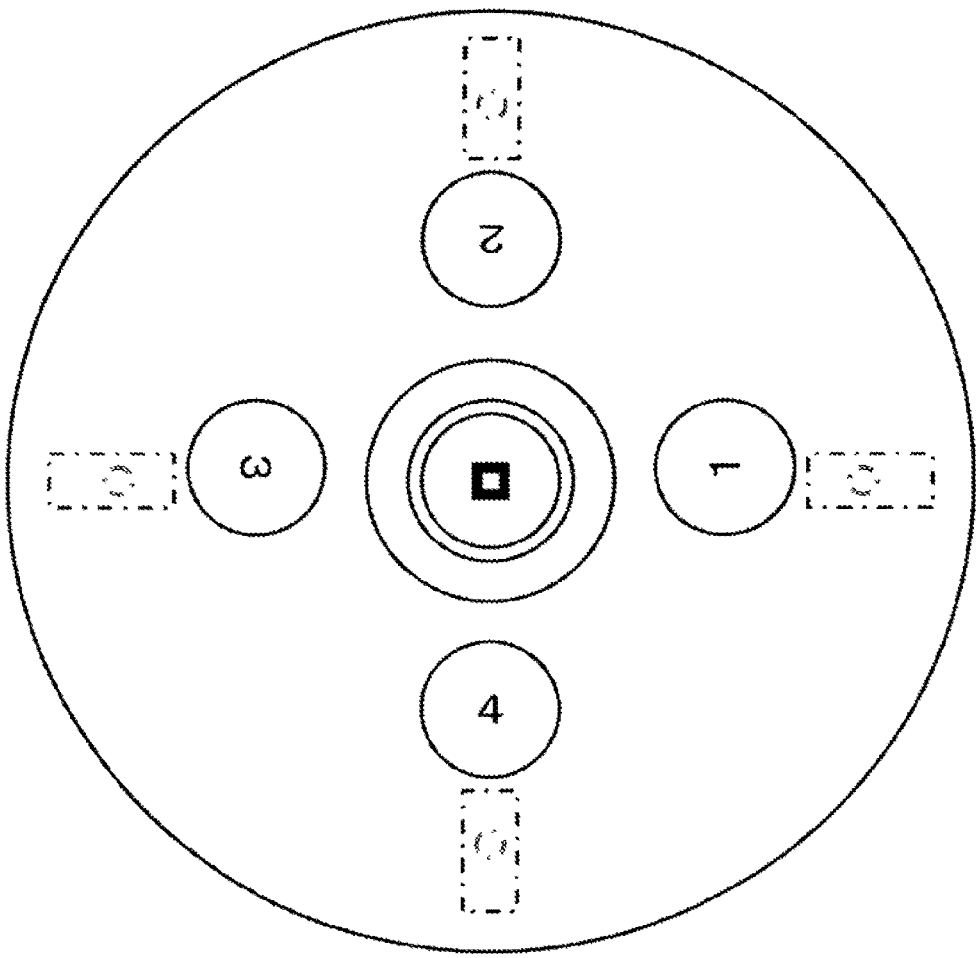

[Fig. 14]

| REAGENT STORAGE UNIT REAGENT INSTALLATION POSITION NUMBER | REAGENT NAME | REMAINING AMOUNT OF REAGENT [ml] | TERM OF VALIDITY | ANALYSIS ITEM | COORDINATE POSITION X, Y, Z |
|---|---|---|---|---|---|
| 1 | REAGENT A | 400 | 2015/1/10 | AST | 200,100,500 |
| 2 | REAGENT B | 350 | 2015/2/10 | ALT | 100,200,500 |
| 3 | REAGENT C | 200 | 2015/1/20 | ALP | 200,300,500 |
| 4 | REAGENT D | 450 | 2015/1/13 | AMY | 300,200,500 |

511,512

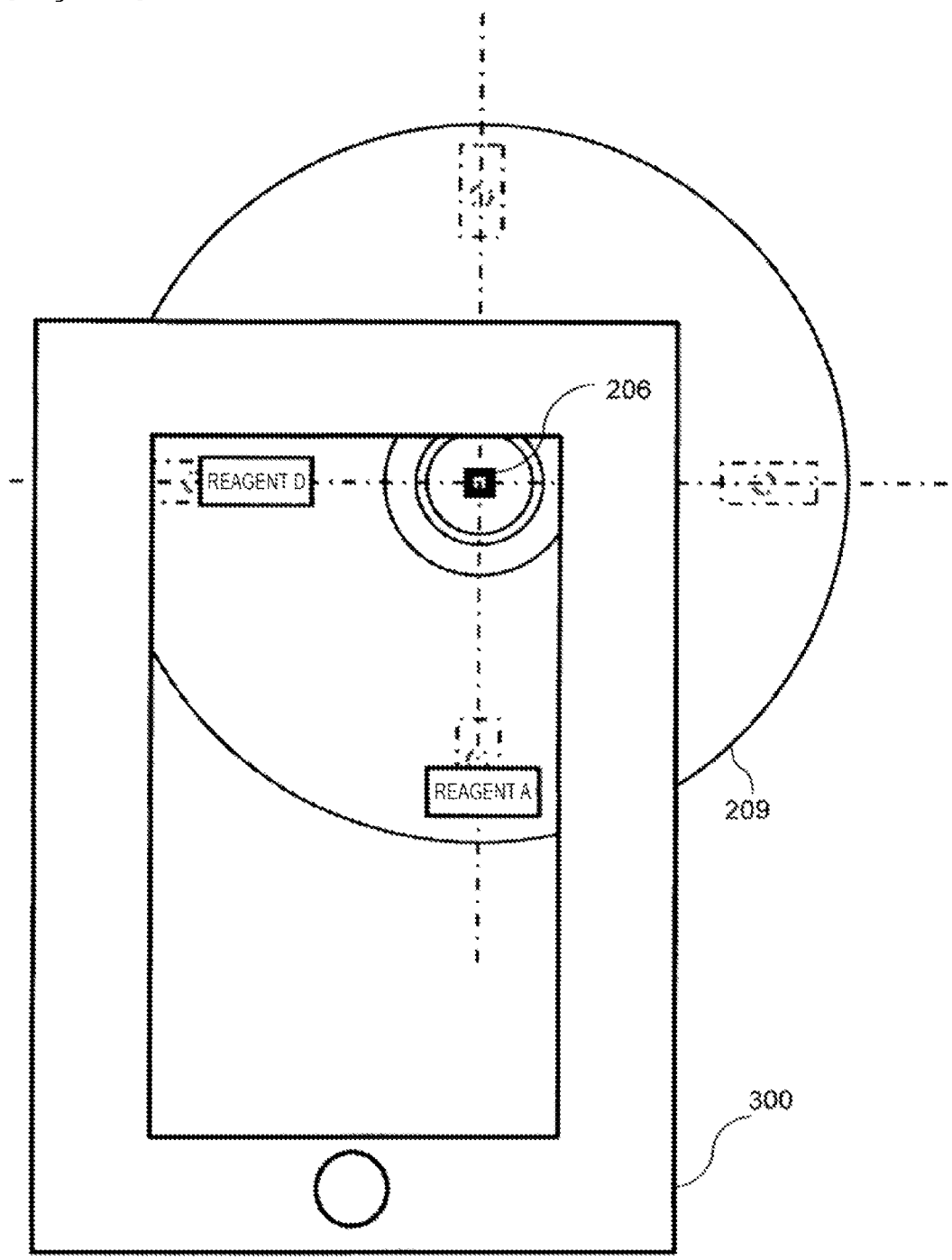
[Fig. 15]

[Fig. 16]
| TWO-DIMENSIONAL CODE ID | PART NAME | COORDINATE POSITION X, Y, Z |
|---|---|---|
| 0001 | REAGENT STORAGE UNIT | 200,200,500 |
509
[Fig. 17]
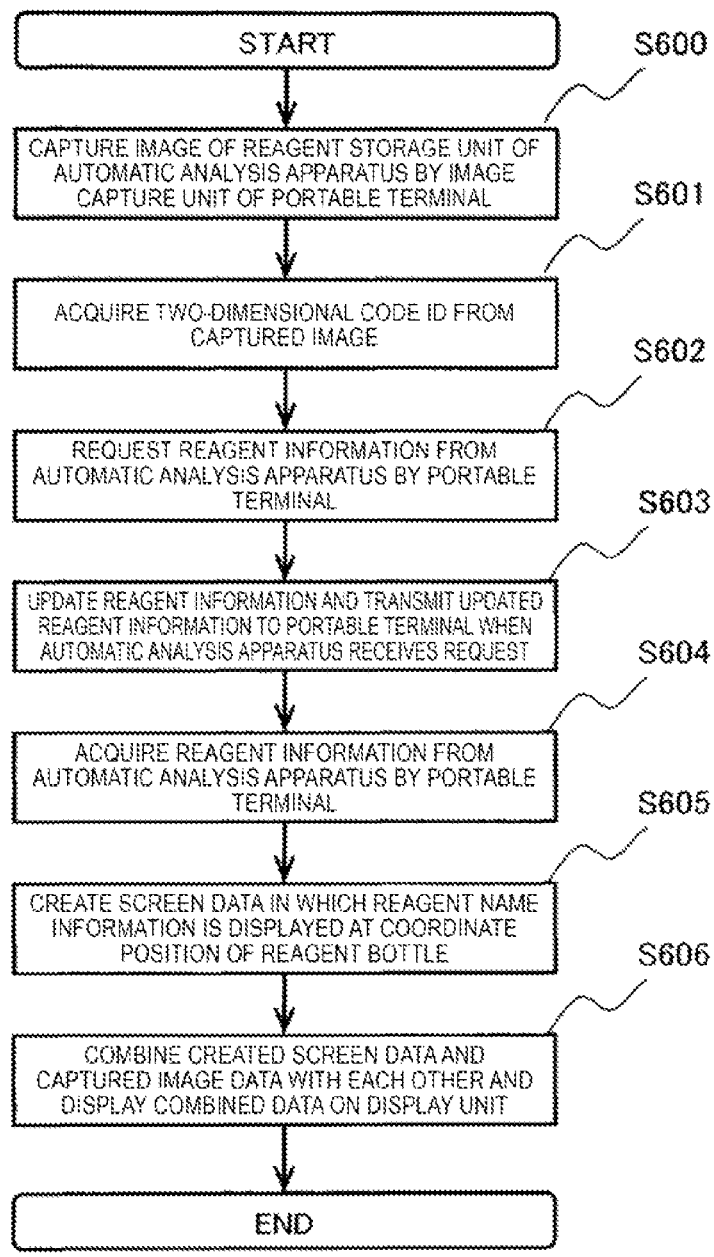

[Fig. 18]
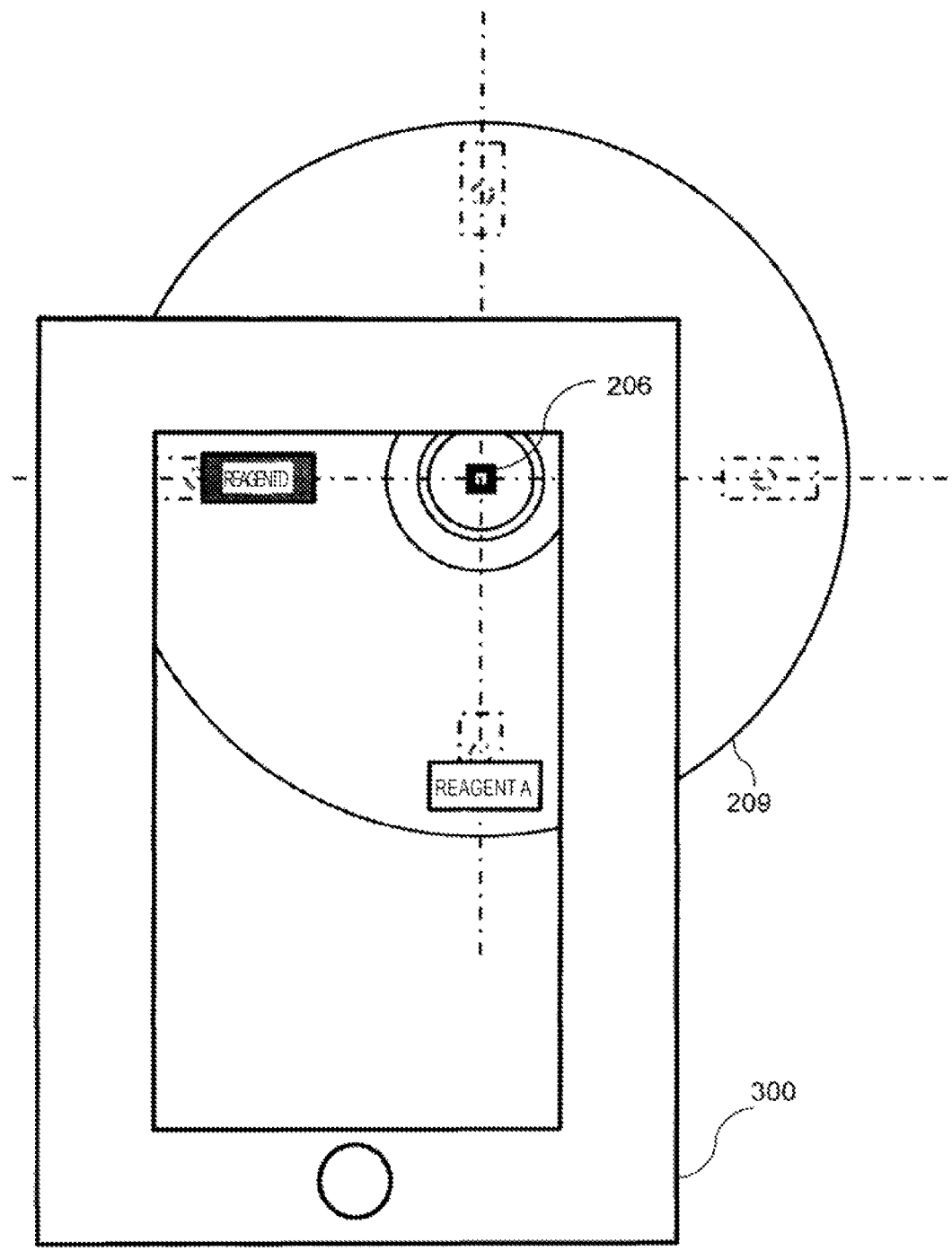

AUTOMATIC ANALYSER

TECHNICAL FIELD

The present invention relates to an automatic analyser.

BACKGROUND ART

As an example of an automatic analyser capable of improving working efficiency during the setting or replacement of a reagent bottle and reducing the erroneous installation of the reagent bottle, PTL 1 discloses an automatic analyser including a reagent refrigerator that fixedly holds and keeps plurality of reagent bottles, a device that reads reagent bottle information on the reagent bottle, a unit that stores the reagent bottle information, a unit that manages a remaining amount of reagent in the reagent bottle, and a display lamp that displays a reagent bottle setting position or a unit that displays the reagent bottle setting position in numerals.

CITATION LIST

Patent Literature

PTL 1: Japanese Patent No. 3314629

SUMMARY OF INVENTION

Technical Problem

In the automatic analyser, a reagent used for analysis is held in a state of being accommodated in a reagent bottle and being kept cold in a reagent storage.

Regarding the reagent, a term of validity is determined for each reagent bottle, and thus a reagent exceeding the determined term cannot be used for analysis. Regarding the reagent, an item capable of being analyzed is determined for each reagent, and thus the reagent cannot be used for the analysis of items other than the determined item. Further, a predetermined amount of reagent is required to be consumed for each analysis, but analysis cannot be performed in a case where the amount of reagent within the reagent bottle is less than a predetermined amount.

For this reason, it is necessary to manage the term of validity, use item, amount, and the like of a reagent held in the automatic analyser in order to perform analysis by the automatic analyser. A general automatic analyser includes a reagent management screen through which a user can confirm reagent information, in order to manage a reagent held in the automatic analyser. Here, the reagent information includes a reagent name, a reagent bottle installation position, a remaining amount of reagent, the term of validity, an analysis item, and the like. The user confirms the reagent information through the reagent management screen to install a necessary reagent bottle or remove an unnecessary reagent bottle.

In recent years, in an automatic analyser, the number of reagent bottles capable of being held in a reagent storage has increased in order to increase the number of items capable of being simultaneously analyzed. Further, the automatic analyser required to perform analysis at high speed and in large quantities includes a plurality of analysis mechanisms and reagent storages, and thus the number of reagent bottles capable of being held in the automatic analyser has increased. In this manner, the number of reagent bottles capable of being held in the automatic analyser has increased, and thus a user has a difficulty in finding a specific reagent bottle.

Here, when the user attempts to confirm reagent information through a reagent management screen and find the specific reagent bottle, a human error of finding the wrong reagent bottle may occur.

For example, when a monitor displaying the reagent management screen and the reagent storage having the reagent bottle installed therein are physically distant from each other, the user needs to move from the front of the monitor to the front of the reagent storage until the user confirms the reagent information on the monitor and then finds the reagent bottle, and thus the user cannot confirm the reagent information when the user is in front of the reagent storage. On the other hand, there is a method of printing the reagent information on a sheet and confirming reagent information from printed matter in front of the reagent storage. However, a human error of finding the wrong reagent bottle due to an erroneous use of a sheet having past reagent information printed thereon may occur. In addition, a monitor and a reagent bottle cannot simultaneously be visually recognized in spite of a short physical distance between a monitor and a reagent storage, and thus a human error of finding the wrong reagent bottle may occur.

With respect to such a problem, in PTL 1 described above, when there is a reagent bottle that a user attempts to find, it is possible to reduce a human error of erroneous finding by providing a display lamp in the vicinity of the reagent bottle and turning on the display lamp in the vicinity of the reagent bottle. However, in the method of PTL 1, it is necessary to install the number of display lamps corresponding to the number of reagent bottles, and the number of display lamps also increases in the automatic analyser in which the number of reagent bottles held increases, which results in a problem in that an installation space, an installation cost, and a maintenance cost increase.

Consequently, a virtual display lamp is provided in the vicinity of the reagent bottle using AR technology, and it is considered that when there is a reagent bottle that a user attempts to find, the virtual display lamp in the vicinity of the reagent bottle is turned on. Accordingly, hardware related to the display lamp is not required, and thus an installation space, an installation cost, and a maintenance cost related to the display lamp are not required.

Meanwhile, augmented reality (AR) is technology for adding information corresponding to the real world to an image obtained by capturing the real world. One of the elements of AR is the alignment of a reality space and a virtual space. This technology is technology capable of adding correct information to a captured image at a correct position and in a correct shape, and various methods are disclosed.

For example, the various methods include a model base alignment method of preparing a three-dimensional model of a target object and finding a similar shape from a captured image, and a marker base alignment method of preparing a sign easy to recognize and finding the prepared sign from a captured image. In the marker base alignment method, ARToolkit is known as a software library that finds the prepared sign from the captured image and calculates a positional relationship between the captured position and the sign (see ARToolKit, http://www.hitl.washington.edu/artoolkit/ and the like).

However, in a case where there is an attempt to provide the virtual display lamp in the vicinity of the reagent bottle using the AR technology, it is necessary to visually recognize the reagent bottle from the outside. However, a general reagent storage is provided with a lid, and thus it is not possible to visually recognize a reagent bottle from the outside. As disclosed in PTL 1, in a case where a reagent bottle is installed at a fixed position at all times, it is possible to ascertain the position of the reagent bottle even when the reagent bottle is not visually recognizable from the outside. However, in an automatic analyser having movement mechanism such as the rotation of a reagent storage itself, the position of a reagent bottle changes, and thus it is not possible to ascertain the position of the reagent bottle when the reagent bottle is visually unrecognizable from the outside.

The invention provides an automatic analyser capable of improving working efficiency at the time of finding a reagent bottle within a reagent storage unit which is visually unrecognizable from the outside, and reducing a human error of finding the wrong reagent bottle.

Solution to Problem

In order to solve the above-described problem, for example, configurations described in claims are adopted.

The invention includes a plurality of means for solving the above-described problem. As an example, there is provided an automatic analyser that dispenses a sample and a reagent to each of a plurality of reaction vessels to react the sample and the reagent with each other and measures a liquid obtained by reacting the sample and the reagent with each other, the automatic analyser including a reagent storage unit that holds a reagent bottle accommodating the reagent, a two-dimensional code which is attached to any position within the automatic analyser, an image capture unit that captures images of the reagent storage unit and the two-dimensional code, an information acquisition unit that acquires coordinate position information of the two-dimensional code within the automatic analyser, coordinate position information of the reagent bottle held within the reagent storage, and reagent information of the held reagent, an image processing unit that identifies the two-dimensional code captured by the image capture unit to specify coordinate position coordinate in the captured image of the two-dimensional code, converts a coordinate system of the captured image obtained by the image capture unit into a coordinate system of the two-dimensional code on the basis of the coordinate position information of the two-dimensional code which is acquired by the information acquisition unit, and specifies a position of the reagent bottle on the captured image on the basis of the converted coordinate system of the captured image, the coordinate position information of the reagent bottle which is acquired by the information acquisition unit, and the reagent information, and a portable terminal that includes a display unit displaying the reagent information regarding the reagent bottle at the position of the reagent bottle on the captured image which is specified by the image processing unit.

Advantageous Effects of Invention

According to the invention, it is possible to improve working efficiency at the time of finding a reagent bottle within a reagent storage unit which is visually unrecognizable from the outside, and reducing a human error of finding a wrong reagent bottle.

Problems, configurations, and effects other than those described above will be clarified by the following description of embodiments.

BRIEF DESCRIPTION OF DRAWINGS

FIG. 1 is a diagram illustrating a configuration of an automatic analyser according to Example 1 of the invention.

FIG. 2 is a diagram illustrating an example of the exterior of a two-dimensional code.

FIG. 3 is a diagram illustrating a configuration of a reagent storage unit of the automatic analyser according to Example 1 when the reagent storage unit is seen from above.

FIG. 4 is a functional block diagram of the automatic analyser according to Example 1.

FIG. 5 is a diagram illustrating an example of a motor information table included in the automatic analyser according to Example 1.

FIG. 6 is a diagram illustrating an example of a reagent storage coordinate position information table included in the automatic analyser according to Example 1 when a rotation angle is 0 degrees.

FIG. 7 is a diagram illustrating the exterior of the reagent storage unit in the automatic analyser according to Example 1 when a rotation angle is 0 degrees.

FIG. 8 is a diagram illustrating an example of the reagent storage coordinate position information table included in the automatic analyser according to Example 1 when a rotation angle is 90 degrees.

FIG. 9 is a diagram illustrating the exterior of the reagent storage unit in the automatic analyser according to Example 1 when a rotation angle is 90 degrees.

FIG. 10 is a diagram illustrating an example of the reagent storage coordinate position information table included in the automatic analyser according to Example 1 when a rotation angle is 180 degrees.

FIG. 11 is a diagram illustrating the exterior of the reagent storage unit in the automatic analyser according to Example 1 when a rotation angle is 180 degrees.

FIG. 12 is a diagram illustrating an example of the reagent storage coordinate position information table included in the automatic analyser according to Example 1 when a rotation angle is 270 degrees.

FIG. 13 is a diagram illustrating the exterior of the reagent storage unit in the automatic analyser according to Example 1 when a rotation angle is 270 degrees.

FIG. 14 is a diagram illustrating an example of a first reagent information table and a second reagent information table included in the automatic analyser according to Example 1.

FIG. 15 is a diagram illustrating the exterior of the reagent storage unit in the automatic analyser according to Example 1 illustrated in FIG. 3 when seen over a portable terminal, and is an example of a screen displayed on a display unit.

FIG. 16 is a diagram illustrating an example of a two-dimensional code information table included in the automatic analyser according to Example 1.

FIG. 17 is a diagram illustrating an example of a flow chart of a process of giving reagent information to an image captured by the portable terminal and displaying the reagent information, the process being executed by the automatic analyser according to Example 1.

FIG. 18 is a diagram illustrating the exterior of a reagent storage unit of an automatic analyser according to Examples 2 and 3 when seen over a portable terminal.

DESCRIPTION OF EMBODIMENTS

Hereinafter, examples of an automatic analyser of the invention will be described with reference to the accompanying drawings.

Example 1

Example 1 of the automatic analyser of the invention will be described with reference to FIGS. 1 to 17.

FIG. 1 is an example of a diagram illustrating a configuration of the automatic analyser according to this example.

In FIG. 1, an automatic analyser 100 includes a processing unit 101, a bus 102, a wireless transmission unit 103, a wireless reception unit 104, a storage unit 106, an input unit 107, a mechanism control unit 111, and a mechanism unit 200.

The processing unit 101, which is a unit executing programs stored in the storage unit 106 to control respective components and performing various computational processes, is constituted by a central processing unit (CPU) or the like. In addition, the processing unit 101 is connected to the wireless transmission unit 103, the wireless reception unit 104, the storage unit 106, and the mechanism control unit 111 through the bus 102.

The wireless transmission unit 103, which is a unit transmitting information using radio waves, transmits information supplied from the processing unit 101 to a portable terminal 300.

The wireless reception unit 104 is a unit that receives information using radio waves, and is a unit that receives information supplied to the processing unit 101 from the portable terminal 300.

The storage unit 106, which is a unit used to permanently store programs and data, is constituted by a hard disk or the like. The storage unit 106 stores information supplied from the processing unit 101 under the control of the processing unit 101. In addition, the storage unit 106 supplies information recorded in the processing unit 101 under the control of the processing unit 101.

The input unit 107, which is a unit inputting information supplied from an operator to the automatic analyser 100, is constituted by a keyboard or the like.

The mechanism control unit 111 controls the operation of each mechanism within the mechanism unit 200 under the control of the processing unit 101.

The mechanism unit 200 includes a sample container 201, a specimen rack 202, a rack transport mechanism 203, a reaction vessel 204, a reaction disk mechanism 205, a thermostat 207, a reagent bottle 208, a reagent storage unit 209, a sample dispensing mechanism 210, a reagent dispensing mechanism 211, a stirring mechanism 212, a cleaning mechanism 213, a light source 214, a photometer 215, an Analog/Digital (A/D) converter 216, and a two-dimensional code for reagent 206.

The sample container 201 is a container into which a sample to be analyzed, such as blood, is put.

The specimen rack 202 is a rack in which a plurality of sample containers 201 can be installed.

The rack transport mechanism 203 includes the specimen rack 202 in which a plurality of sample containers 201 are installed. The rack transport mechanism 203 transports the specimen rack 202 installed therein by its own driving unit under the control of the processing unit 101.

The reaction vessel 204 is a container which a reagent and a sample are put into to react with each other.

The reaction disk mechanism 205 is a mechanism that holds a plurality of reaction vessels 204. In addition, the reaction disk mechanism 205 transports the reaction vessel 204 installed therein to a designated position by the driving unit under the control of the processing unit 101.

The two-dimensional code 206 is an identification index attached to an upper surface side of a cover provided in the reagent storage unit 209 so as to be visually recognized from the outside of the automatic analyser 100. FIG. 2 is an example of the two-dimensional code 206 of FIG. 1. In FIG. 2, the two-dimensional code 206 is a two-dimensional code which is used for ARToolKit. It is possible to recognize the two-dimensional code by a combination of a black frame and a white region within the frame, and to read a two-dimensional code ID by recognizing the pattern of the white region.

The thermostat 207 is a member for maintaining the reaction vessel 204 installed in the reaction disk mechanism 205 at a predetermined temperature, and maintains the reaction vessel 204 at a predetermined temperature under the control of the processing unit 101.

The reagent bottle 208 is a container that accommodates a reagent to be used for analysis.

The reagent storage unit 209 is a mechanism that holds a plurality of reagent bottles 208. In addition, the reagent storage unit 209 transports the reagent bottle 208 installed therein to a designated position by the driving unit under the control of the processing unit 101.

FIG. 3 is an example of a diagram illustrating the exterior of the reagent storage unit 209 when seen from above. As illustrated in FIG. 3, in this example, the reagent storage unit 209 includes four reagent storage unit reagent installation position numbers, four reagent bottles 208, and one two-dimensional code 206. In FIG. 3, circled numbers indicate the reagent storage unit reagent installation position numbers, and are not actually engraved. When the reagent storage unit 209 is rotated, the reagent storage unit reagent installation position numbers and the reagent bottle 208 are rotated in association with the reagent storage unit 209, but the two-dimensional code 206 is configured not to be rotated.

The sample dispensing mechanism 210 is a mechanism that includes a sample dispensing probe and divides a sample into small fixed amounts. The sample dispensing mechanism 210 dispenses a sample, which is put into the sample container 201, into the reaction vessel 204 by a predetermined amount under the control of the processing unit 101.

The reagent dispensing mechanism 211 is a mechanism that includes a reagent dispensing probe and divides a reagent into small fixed amounts. The reagent dispensing mechanism 211 dispenses a reagent, which is put into the reagent bottle 208, into the reaction vessel 204 by a predetermined amount under the control of the processing unit 101.

The stirring mechanism 212 is a mechanism that stirs the reagent and the sample solution, which are put into the reaction vessel 204, and makes a distribution state of components uniform under the control of the processing unit 101.

The cleaning mechanism 213 is a mechanism that draws up a waste liquid and discharges a cleaning liquid. The cleaning mechanism 213 draws up solutions of the reagent and the sample which are put into the reaction vessel 204 under the control of the processing unit 101. In addition, the cleaning mechanism 213 discharges the cleaning liquid into the reaction vessel 204 under the control of the processing unit 101 to clean the reaction vessel 204.

The light source 214, which is a unit emitting light used for the measurement of absorbance, is constituted by a halogen lamp or the like, and emits light under the control of the processing unit 101.

The photometer 215 is a unit receiving the light which is emitted by the light source 214 and has passed through the reaction vessel 204 to measure the absorbance of a solution inside the reaction vessel 204, and is constituted by a spectrophotometer or the like. The photometer 215 transmits information regarding the absorbance to the A/D converter 216 under the control of the processing unit 101.

The A/D converter 216, which is a unit converting an analog signal into a digital signal, converts an analog signal which is input under the control of the processing unit 101 into a digital signal, and then records the converted digital signal in the storage unit 106.

The portable terminal 300 includes a processing unit 301, a bus 302, a wireless transmission unit 303, a wireless reception unit 304, a storage unit 306, an input unit 307, a display unit 308, and an image capture unit 309.

The processing unit 301 executes programs stored in the storage unit 306 to control components, and performs various computational processes. Specifically, the processing unit 301 is constituted by a CPU. In addition, the processing unit 301 is connected to the wireless transmission unit 303, the wireless reception unit 304, the storage unit 306, the display unit 308, and the image capture unit 309 through the bus 302.

The wireless transmission unit 303, which is a unit transmitting information using radio waves, transmits information supplied from the processing unit 301 to the automatic analyser 100.

The wireless reception unit 304, which is a unit receiving information using radio waves, receives information supplied to the processing unit 301 from the automatic analyser 100.

The storage unit 306, which is a unit used to permanently store programs and data, is constituted by a hard disk or the like. The storage unit 306 records information supplied from the processing unit 301 under the control of the processing unit 301. In addition, the storage unit 306 supplies information recorded in the processing unit 301 under the control of the processing unit 301.

The input unit 307, which is a unit inputting information supplied from an operator to the portable terminal 300, is constituted by a touch panel, a numeric keypad, or the like.

The display unit 308, which is a unit outputting information supplied to an operator, is constituted by a display or the like, and displays information supplied from the processing unit 301 under the control of the processing unit 301.

The image capture unit 309, which is a unit used to capture an image of the real world, is constituted by a camera or the like, and captures images of the reagent storage unit 209 and the two-dimensional code 206 to acquire image information under the control of the processing unit 301.

FIG. 4 is an example of a functional block diagram of this example.

In FIG. 4, the automatic analyser 100 includes the processing unit 101, the storage unit 106, the wireless transmission unit 103, and the wireless reception unit 104.

Among these units, the processing unit 101 includes an operation control unit 500, an automatic analyser information transmission unit 501, and a portable terminal information reception unit 502.

The operation control unit 500 records rotation angle information of a motor rotating the reagent storage unit in a rotation angle of a motor information table 507 to be described later. In addition, the operation control unit 500 records information regarding a reagent installed in the reagent storage in a remaining amount of reagent of a first reagent information table 511, or the like.

The automatic analyser information transmission unit 501 controls the wireless transmission unit 103 to transmit information of the first reagent information table 511 to be described later to the portable terminal 300.

The portable terminal information reception unit 502 controls the wireless reception unit 104 to receive a signal for requesting reagent information from the portable terminal 300. In addition, the portable terminal information reception unit 502 acquires rotation angle information of a reagent storage unit rotation motor from the motor information table 507, and acquires coordinate position information for each reagent storage unit reagent installation position number from a reagent storage coordinate position information table 510 in accordance with a rotation angle. The portable terminal information reception unit 502 records coordinate position information in a coordinate position of the table to create the first reagent information table 511 and store the created first reagent information table 511 in the storage unit 106.

The storage unit 106 includes the motor information table 507, the reagent storage coordinate position information table 510, and the first reagent information table 511.

FIG. 5 is an example of the motor information table 507 illustrated in FIG. 4. The motor information table 507 includes motor number information, motor name information, and rotation angle information. Among these information, a number previously given to the motor is recorded in the motor number information. A name previously given to the motor is recorded in the motor name information. Information supplied by the operation control unit 500 is recorded in the rotation angle information.

FIG. 6 is an example of the reagent storage coordinate position information table 510 when a rotation angle is 0 degrees, and FIG. 7 illustrates a relationship between the rotation angle and reagent storage unit reagent installation position numbers at that time. FIG. 8 is an example of the reagent storage coordinate position information table 510 when a rotation angle is 90 degrees, and FIG. 9 illustrates the reagent storage unit and reagent storage unit reagent installation position numbers at that time. FIG. 10 is an example of the reagent storage coordinate position information table 510 when a rotation angle is 180 degrees, and FIG. 11 illustrates the reagent storage unit and reagent storage unit reagent installation position numbers at that time. FIG. 12 is an example of the reagent storage coordinate position information table 510 when a rotation angle is 270 degrees, and FIG. 13 illustrates the reagent storage unit and reagent storage unit reagent installation position numbers at that time.

In FIGS. 6 to 12, the reagent storage coordinate position information table 510 includes a reagent storage unit position sign and a reagent storage unit coordinate position. Among these, a sign indicating the position of the reagent storage unit which is determined in advance is recorded in the reagent storage unit position sign. Coordinate information of the position indicated by the reagent storage unit position sign is recorded in the reagent storage unit coordinate position. The coordinate position information is information to be acquired from a design drawing such as a CAD drawing.

As illustrated in FIGS. 6, 8, 10, and 12, the reagent storage unit coordinate position changes depending on a rotation angle of the reagent storage unit. For example, a positional relationship as illustrated in FIG. 7 is obtained when the rotation angle is 0 degrees, and the reagent storage coordinate position information table 510 is as illustrated in FIG. 6. A positional relationship as illustrated in FIG. 9 is obtained when the rotation angle is 90 degrees, and the reagent storage coordinate position information table 510 changes as illustrated in FIG. 8. A positional relationship as illustrated in FIG. 11 is obtained when the rotation angle is 180 degrees, and the reagent storage coordinate position information table 510 changes as illustrated in FIG. 10. A positional relationship as illustrated in FIG. 13 is obtained when the rotation angle is 270 degrees, and the reagent storage coordinate position information table 510 changes as illustrated in FIG. 12.

FIG. 14 is an example of the first reagent information table 511 illustrated in FIG. 4 and a second reagent information table 512 to be described later.

As illustrated in FIG. 14, the first reagent information table 511 and the second reagent information table 512 include a reagent storage unit reagent installation position number, a reagent name, a remaining amount of reagent, a term of validity, an analysis item, and a coordinate position.

In FIG. 14, a number of the reagent storage unit which is determined in advance is recorded in the reagent storage unit reagent installation position number. The name of a reagent accommodated in the reagent bottle installed in the reagent storage unit is recorded in the reagent name by the operation control unit 500. A remaining amount of reagent accommodated in the reagent bottle installed in the reagent storage unit is recorded in the remaining amount of reagent by the operation control unit 500. The term of validity of a reagent accommodated in the reagent bottle installed in the reagent storage unit is recorded in the term of validity by the operation control unit 500. An item name determined for the reagent accommodated in the reagent bottle installed in the reagent storage unit is recorded in the analysis item by the operation control unit 500. The coordinate position of a reagent storage unit reagent installation position which is determined in advance is recorded in the coordinate position.

Referring back to FIG. 4, the portable terminal 300 includes the processing unit 301, the storage unit 306, the wireless transmission unit 303, the wireless reception unit 304, the image capture unit 309, and the display unit 308.

The processing unit 301 includes a portable terminal information transmission unit 503, an automatic analyser information reception unit 504, and an image processing unit 505.

The portable terminal information transmission unit 503 controls the wireless transmission unit 303 to transmit a signal for requesting reagent information from the automatic analyser 100.

The automatic analyser information reception unit 504 controls the wireless reception unit 304 to receive information of the first reagent information table 511 from the automatic analyser 100. In addition, the automatic analyser information reception unit 504 records the received information of the first reagent information table 511 in the storage unit 306 as the second reagent information table 512.

The image processing unit 505 controls the image capture unit 309 to capture an image of the reagent storage unit 209 including the two-dimensional code 206. The image processing unit 505 recognizes the two-dimensional code 206 from the captured image to read a two-dimensional code ID using AR technology. After that, coordinate position information corresponding to the two-dimensional code ID read from the two-dimensional code information table 509 is acquired. In addition, position information of the two-dimensional code 206 recognized earlier is acquired by a coordinate system centering on the image capture unit 309 on the basis of AR technology.

Further, the image processing unit 505 combines coordinate position information of the two-dimensional code 206 acquired from the two-dimensional code information table 509 and coordinate position information of the two-dimensional code 206 acquired using AR technology with each other to correct the coordinate system. Consequently, images displaying the pieces of information, acquired from the second reagent information table 512, in accordance with the respective coordinate positions are created and output to the display unit 308 in combination with the captured image.

The display unit 308 displays a combination of the captured image processed by the image processing unit 505 and the reagent information. For example, a screen as illustrated in FIG. 15 is displayed on the display unit 308. Meanwhile, FIG. 15 is an example of a diagram illustrating the exterior of the reagent storage unit 209 displayed on the display unit 308.

Referring back to FIG. 4, the storage unit 306 includes the two-dimensional code information table 509 and the second reagent information table 512.

FIG. 16 is an example of the two-dimensional code information table 509 illustrated in FIG. 4. In FIG. 16, the two-dimensional code information table 509 includes two-dimensional code ID information, part name information, and coordinate position information. Among these information, an ID given to the two-dimensional code 206 in advance is recorded in the two-dimensional code ID information. A part having the two-dimensional code 206 attached thereto in advance is recorded in the part name information. A coordinate position having the two-dimensional code 206 attached thereto in advance is recorded in the coordinate position.

Next, a description will be given of a method of analyzing the concentration of a predetermined component in a specimen using the automatic analyser according to this example. Basically, analysis is performed by controlling respective components by the processing unit 101 and controlling each mechanism of the automatic analyser 100.

First, the processing unit 101 controls the rack transport mechanism 203 to transport the specimen rack 202 installed in the rack transport mechanism 203 to a position immediately below the sample dispensing probe of the sample dispensing mechanism 210.

Next, the processing unit 101 controls the sample dispensing mechanism 210 to draw up a sample which is put into the sample container 201 installed in the specimen rack 202 by a predetermined amount and discharges the sample into the reaction vessel 204 installed in the reaction disk mechanism 205.

Next, the processing unit 101 controls the reaction disk mechanism 205 to transport the reaction vessel 204 having a sample put thereinto to a position immediately below the reagent dispensing mechanism 211. At the same time, the processing unit 101 controls the reagent storage unit 209 to transport the predetermined reagent bottle 208 to a position immediately below the reagent dispensing mechanism 211.

Next, the processing unit 101 controls the reagent dispensing mechanism 211 to suck a reagent which is put into the reagent bottle 208 by a predetermined amount and discharges the reagent into the reaction vessel 204 which the sample discharged before is put into.

Next, the processing unit 101 controls the reaction disk mechanism 205 to transport the reaction vessel 204 having solutions of the reagent and the sample put thereinto to the position of the stirring mechanism 212.

Next, the processing unit 101 controls the stirring mechanism 212 to stir solutions of the reagent and the sample which are put into the reaction vessel 204.

Next, the processing unit 101 controls the reaction disk mechanism 205 to transport the reaction vessel 204 having solutions of the reagent and the sample put thereinto to the position of the photometer 215.

Next, the processing unit 101 controls the light source 214 to generate light. At the same time, the processing unit 101 controls the photometer 215 to transmit information of measured absorbance to the A/D converter 216. Further, at the same time, the processing unit 101 controls the A/D converter 216 to record information of absorbance converted into a digital signal in the storage unit 106 and computationally calculates the concentration of a predetermined component in a specimen.

Next, the processing unit 101 controls the reaction disk mechanism 205 to transport the reaction vessel 204 having solutions of the reagent and the sample put thereinto to the position of the cleaning mechanism 213.

Next, the processing unit 101 controls the cleaning mechanism 213 to clean the reaction vessel 204 having solutions of the reagent and the sample put thereinto.

Next, a flow of the creating of a screen displayed on the display unit 308 in this example will be described with reference to FIG. 17. FIG. 17 is an example of a flow chart of the processing of each function illustrated in FIG. 4.

First, in step S600, the portable terminal 300 captures an image of the reagent storage unit 209 by the image capture unit 309 so as to include the two-dimensional code 206 under the control of the image processing unit 505.

Subsequently, in step S601, the portable terminal 300 acquires a two-dimensional code ID from the image captured in step S600 using AR technology under the control of the image processing unit 505.

Subsequently, in step S602, the portable terminal 300 recognizes that an image of the reagent storage unit 209 is captured, from the two-dimensional code ID acquired in step S601 and the two-dimensional code information table 509 stored in the storage unit 306 under the control of the image processing unit 505. In addition, the portable terminal 300 transmits a signal for requesting reagent information from the wireless transmission unit 303 to the automatic analyser 100 under the control of the portable terminal information transmission unit 503.

Subsequently, in step S603, the automatic analyser 100 receives a signal for requesting reagent information from the wireless reception unit 104, from the portable terminal 300 under the control of the portable terminal information reception unit 502. After this signal is received, the automatic analyser 100 acquires rotation angle information of the motor rotating the reagent storage unit from the motor information table 507 under the control of the portable terminal information reception unit 502. In addition, the automatic analyser 100 acquires coordinate position information for each reagent installation position number corresponding to the rotation angle information of the motor from the reagent storage coordinate position information table 510 under the control of the portable terminal information reception unit 502. Further, the automatic analyser 100 records the acquired coordinate position information in the table to create the first reagent information table 511 under the control of the portable terminal information reception unit 502. The automatic analyser 100 transmits information of the first reagent information table 511 to the portable terminal 300 by using the wireless transmission unit 103 under the control of the automatic analyser information transmission unit 501.

Subsequently, in step S604, the portable terminal 300 receives the information of the first reagent information table 511 from the automatic analyser 100 by using the wireless reception unit 304 under the control of the automatic analyser information reception unit 504. Thereafter, the portable terminal 300 records the received first reagent information table 511 in the storage unit 306 as the second reagent information table 512 under the control of the automatic analyser information reception unit 504.

Subsequently, in step S605, the portable terminal 300 converts the coordinate system of the image capture unit 309 into a coordinate system of the two-dimensional code 206 using AR technology from the image captured in step S600 under the control of the image processing unit 505. In addition, coordinate position information is acquired from the second reagent information table 512 under the control of the image processing unit 505. This coordinate position information of the reagent bottle is a coordinate position in the coordinate system of the two-dimensional code 206. Thereafter, reagent name information is acquired from the second reagent information table 512 to create screen data displayed at a coordinate position of the reagent bottle under the control of the image processing unit 505.

Subsequently, in step S606, the portable terminal 300 combines the screen data created in step S605 and the image captured in step S601 with each other and displays the combined resultant on the display unit 308 under the control of the image processing unit 505.

Next, effects of this example will be described.

In Example 1 described above of the automatic analyser of the invention, the two-dimensional code 206 is attached to any position of the automatic analyser 100, for example, a location (an upper surface side of a cover, or the like) of the reagent storage unit 209 which is visually recognizable from the outside, and the coordinate position of the two-dimensional code 206 in the coordinate system of the two-dimensional code 206 and coordinate information of the installation position of the reagent bottle 208 are held. After that, an image of the two-dimensional code 206 is captured by the portable terminal 300 so that the coordinate system of the image capture unit 309 of the portable terminal 300 is converted into the coordinate system of the two-dimensional code 206 using AR technology. The coordinate information of the installation position of the reagent bottle 208 in the coordinate system of the two-dimensional code 206 is regarded as positional coordinates in the captured image on the basis of conversion information, thereby ascertaining the position of the reagent bottle 208 on the captured image. The ascertained position is displayed on the display unit 308.

Thereby, when the two-dimensional code 206 recognizable from the outside by the portable terminal 300 is read, it is possible to ascertain the position of the reagent bottle 208, which is unrecognizable from the outside, in a form close to real time, and to reduce a human error of finding the wrong reagent bottle.

Meanwhile, in this example, the reagent name is displayed as information displayed in the vicinity of the reagent bottle. However, information to be displayed is not limited thereto, and various information regarding the reagent bottle can be displayed.

In addition, in this example, an example of a case where identification is performed by the marker base alignment method using a two-dimensional code has been described.

However, identification may be performed by a model base alignment method, or may be performed by any of other methods.

Further, in this example, a description has been given on the assumption that the number of reagent storage unit reagent installation positions is four, the number of reagent storage unit rotation angles is four, and the number of reagent bottles is four. However, the invention is not limited thereto, and the numbers may be appropriately changed depending on the specifications of the automatic analyser.

In addition, in this example, an example of the automatic analyser performing the measurement of absorbance has been described, but the automatic analyser is not limited thereto.

Further, in this example, a description of an example has been given in which the invention is applied to an automatic analyser performing biochemical analysis such as for blood as the automatic analyser. However, an automatic analyser to which the invention can be applied is not limited to a biochemical analyser, and the invention can also be applied to other types of automatic analyseres, such as an immunity analyser performing immunological analysis, which includes one or more reagent storage units.

Example 2

Example 2 of the automatic analyser of the invention will be described with reference to FIG. 18. The same components as those in FIGS. 1 to 17 will be denoted by the same reference numerals and signs, and a description thereof will not be repeated. The same is true of the following examples.

In a case where it is known that the reagent bottle 208 has to be removed due to a reason such as the excess of the term of validity or a remaining amount being less than a predetermined amount, among the reagent bottles 208 held by the automatic analyser 100, the automatic analyser of this example highlights reagent information of the reagent bottle 208 desired to be removed through coloration, among pieces of reagent information displayed on the captured image displayed on the display unit 308.

For example, in a case where a reagent D is highlighted due to a reason such as the expiration of the term of validity or the shortage of a remaining amount, the image processing unit 505 performs control of highlighting the reagent D as illustrated in FIG. 18. Meanwhile, in this case, the reason for the highlighting (the expiration of the term of validity, the shortage of a remaining amount, or the like) may also be highlighted.

Also in Example 2 of the automatic analyser of the invention, substantially the same effects as those in Example 1 of the automatic analyser described above are obtained.

Further, since a reagent to be colored is highlighted, it is possible to further easily find a reagent bottle, to further improve working efficiency, and to further reduce a human error of finding the wrong reagent bottle.

Example 3

Example 3 of the automatic analyser of the invention will be described below.

In a case where a user selects a specific reagent bottle on a reagent management screen of the automatic analyser of this example, the automatic analyser highlights reagent information of the reagent bottle through coloration among pieces of reagent information displayed on a captured image. Also in the automatic analyser of this example, a screen as illustrated in FIG. 18 is displayed.

Also in Example 3 of the automatic analyser of the invention, substantially the same effects as those in Example 2 of the automatic analyser described above are obtained.

Others

Meanwhile, the invention is not limited to the above-described examples, and various modifications are included therein. The above-described examples have been explained in detail in order to facilitate the understanding of the invention, and the invention is not necessarily limited to those including all configurations described. In addition, a portion of the configuration of a certain example can be replaced by the configuration of another example, and the configuration of another example can be added to the configuration of a certain example. Further, it is possible to perform the addition, deletion, and replacement of another configuration with respect to a portion of the configuration of each example.

REFERENCE SIGNS LIST

100: AUTOMATIC ANALYSER
101: PROCESSING UNIT
102: BUS
103: WIRELESS TRANSMISSION UNIT
104: WIRELESS RECEPTION UNIT
106: STORAGE UNIT
107: INPUT UNIT
111: MECHANISM CONTROL UNIT
200: MECHANISM UNIT
201: SAMPLE CONTAINER
202: SPECIMEN RACK
203: RACK TRANSPORT MECHANISM
204: REACTION VESSEL
205: REACTION DISK MECHANISM
206: TWO-DIMENSIONAL CODE
207: THERMOSTAT
208: REAGENT BOTTLE
209: REAGENT STORAGE UNIT
210: SAMPLE DISPENSING MECHANISM
211: REAGENT DISPENSING MECHANISM
212: STIRRING MECHANISM
213: CLEANING MECHANISM
214: LIGHT SOURCE
215: PHOTOMETER
216: A/D CONVERTER
300: PORTABLE TERMINAL
301: PROCESSING UNIT
302: BUS
303: WIRELESS TRANSMISSION UNIT
304: WIRELESS RECEPTION UNIT
306: STORAGE UNIT
307: INPUT UNIT
308: DISPLAY UNIT
309: IMAGE CAPTURE UNIT
500: OPERATION CONTROL UNIT
501: AUTOMATIC ANALYSER INFORMATION TRANSMISSION UNIT
502: PORTABLE TERMINAL INFORMATION RECEPTION UNIT
503: PORTABLE TERMINAL INFORMATION TRANSMISSION UNIT
504: AUTOMATIC ANALYSER INFORMATION RECEPTION UNIT
505: IMAGE PROCESSING UNIT
507: MOTOR INFORMATION TABLE

509: TWO-DIMENSIONAL CODE INFORMATION TABLE
510: REAGENT STORAGE COORDINATE POSITION INFORMATION

Table

511: FIRST REAGENT INFORMATION TABLE
512: SECOND REAGENT INFORMATION TABLE

The invention claimed is:

1. An automatic analyser that dispenses a sample and a reagent to each of a plurality of reaction vessels to react the sample and the reagent with each other and measures a liquid obtained by reacting the sample and the reagent with each other, the automatic analyser comprising:
   a reagent storage unit that holds a reagent bottle accommodating the reagent;
   a two-dimensional code which is attached to any position within the automatic analyser;
   an image capture unit that captures images of the reagent storage unit and the two-dimensional code;
   an information acquisition unit that acquires coordinate position information of the two-dimensional code within the automatic analyser, coordinate position information of the reagent bottle held within the reagent storage unit, and reagent information of the held reagent;
   an image processing unit that identifies the two-dimensional code captured by the image capture unit to specify coordinate position coordinate in the captured image of the two-dimensional code, converts a coordinate system of the captured image obtained by the image capture unit into a coordinate system of the two-dimensional code on the basis of the coordinate position information of the two-dimensional code which is acquired by the information acquisition unit, and specifies a position of the reagent bottle on the captured image on the basis of the converted coordinate system of the captured image, the coordinate position information of the reagent bottle which is acquired by the information acquisition unit, and the reagent information; and
   a portable terminal that includes a display unit displaying the reagent information regarding the reagent bottle at the position of the reagent bottle on the captured image which is specified by the image processing unit.

2. The automatic analyser according to claim 1, wherein the image capture unit, the information acquisition unit, and the image processing unit are provided in the portable terminal.

3. The automatic analyser according to claim 1, wherein the image processing unit controls to highlight information to be highlighted in the reagent information regarding the reagent bottle to be displayed on the display unit.

\* \* \* \* \*